United States Patent [19]

Young

[11] Patent Number: 4,694,823
[45] Date of Patent: Sep. 22, 1987

[54] NECK AND FACIAL LIFT BAND ASSEMBLY

[76] Inventor: Marilyn M. Young, 430 57th Pl. NE., Minneapolis, Minn. 55432

[21] Appl. No.: 832,382

[22] Filed: Feb. 24, 1986

[51] Int. Cl.[4] .............................................. A61F 5/00
[52] U.S. Cl. .................................. 128/76 B; 2/171.2; 128/164
[58] Field of Search ............... 128/76 B, 76 R, 75, 128/163, 164; 2/171, 171.2, 174

[56] References Cited

U.S. PATENT DOCUMENTS

| | | | |
|---|---|---|---|
| 3,118,443 | 1/1964 | Dykinga | 128/75 |
| 3,572,329 | 3/1971 | De Woskin | 128/76 R |
| 3,776,244 | 12/1973 | Morgan | 128/76 B X |

FOREIGN PATENT DOCUMENTS 403458 10/1924 Fed. Rep. of Germany .... 128/76 B

Primary Examiner—Edgar S. Burr
Assistant Examiner—Moshe I. Cohen
Attorney, Agent, or Firm—John W. Adams

[57] ABSTRACT

Apparatus for supporting chin, neck and facial tissue during sleep which includes a neck-embracing lower attachment portion and an over-the-head criss-cross anchoring portion, the two attachment portions combining to securely anchor tissue engaging support portions for engaging the lower chin and posterior jaw portions to provide substantially uniform lifting on all of the engaged skin and neck areas to prevent and remove neck and facial sagging and wrinkling of the skin.

8 Claims, 5 Drawing Figures

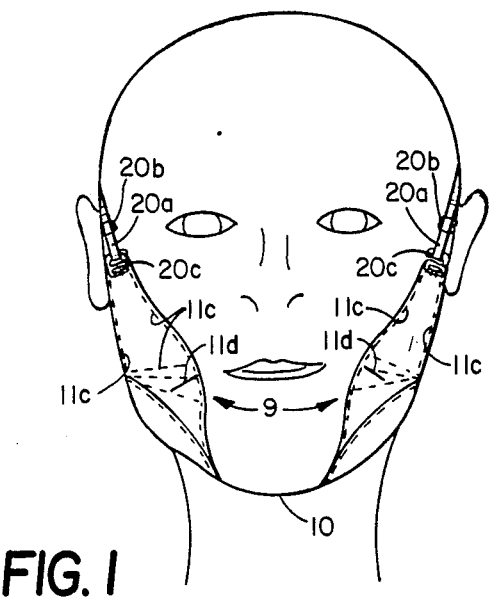
FIG. 1
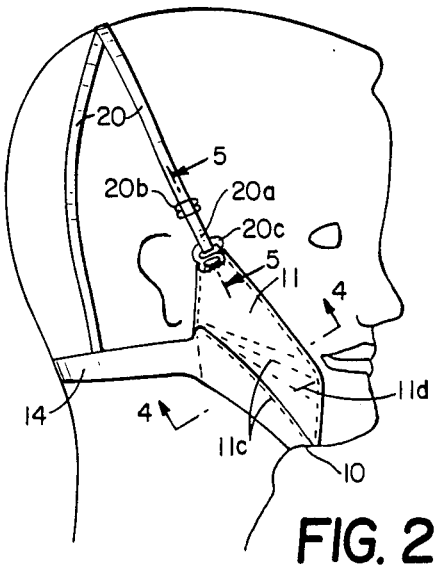
FIG. 2
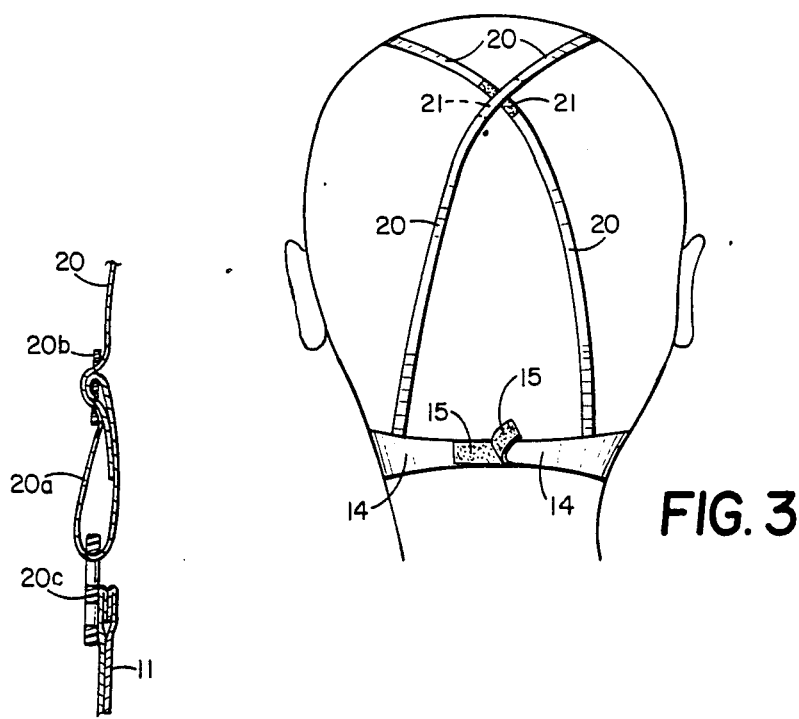
FIG. 3
FIG. 5
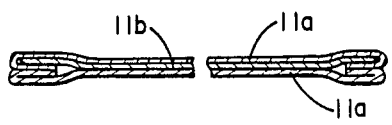
FIG. 4

NECK AND FACIAL LIFT BAND ASSEMBLY

SUMMARY OF THE INVENTION

Many facial beauty aids have been developed over the years to remove and prevent facial wrinkles and sagging of skin on the face and neck. With the present invention, this is accomplished by a yoke assembly which includes a central chin segment and a pair of lateral jaw engaging segments connected together at the front and positively anchored around the neck and over the head-of the wearer to produce the required positioning and tensioning on the engaged skin portions. The lower front chin engaging segment is stretchable providing the necessary contour of the whole assembly and also the necessary stretching and lifting movement of the throat area. The lateral jaw engaging segments are non-stretchable to provide the necessary control and lifting of selected skin areas of the face and neck. The lateral segments are securely anchored by a neck strap and over-the-head straps specifically adjustable to the dimensions of the wearer's head and providing the upwardly desired lifting force to the engaged skin portions.

DESCRIPTION OF THE DRAWINGS

FIG. 1 is a front elevational view of the device embodying this invention;

FIG. 2 is a side elevational view thereof;

FIG. 3 is a back elevational view thereof;

FIG. 4 is a sectional view taken substantially along the line 4—4 of FIG. 2; and FIG. 5 is a sectional view taken substantially along the line 5—5 of FIG. 2.

DETAILED DESCRIPTION OF THE PREFERRED EMBODIMENT

The device illustrated in the accompanying drawings embodies a yoke assembly 9 which includes an under-the-chin segment 10 made from stretchable material and a pair of generally upwardly extending lateral segments 11. The lateral segments 11 are made from a combination of stretchable layers 11a which are a continuation of the stretchable material of segments 10, with a non-stretchable layer 11b laminated therewith as best shown in the sectional view, FIG. 4 to produce the desired non-stretchable segments 11 which extend upwardly to approximately the level of the center of the ears of the wearer. Suitable stitching 11c positively connects the stretchable and non-stretchable laminations at the critical chin engaging area of the lateral segments 11. A pair of take-up darts 11d are provided along the upper edge portions of the segments 11 to conform the inner shape of said segments to the shape of the wearer's face and maintain surface-to-surface contact therewith.

A pair of lower neck surrounding anchoring strap elements 14 are connected to the rear edge portions of the lateral segments 11 to position the strap elements below the ears of the wearer in the desired upper neck surrounding location. Suitable means for positively interconnecting the rear ends of the strap elements 14 are provided such as the mating velcro-type connecting segments 15 which are sufficiently long to provide for substantial adjustment along sufficient overlap to positively anchor the ends of the strap elements 14 together as best shown in FIG. 3.

A pair of over-the-head criss-cross stretchable straps 20 are provided to provide upward tension on the lateral jaw engaging segments 11 as illustrated. In the form shown, the rear ends of the straps 20 are anchored to intermediate portions of the respective neck anchoring strap elements 14 and pass upwardly therefrom in criss-cross relation over the top of the wearer's head for connection to the upper ends of the lateral jaw engaging segments 11. In the form shown, the front ends of the straps 20 are doubled back upon themselves to form adjustable loops 20a, each has an adjustment slide 20b of conventional design. A hook 20c is connected to each of the upper ends of the segments 11 as illuslrated and is removably anchored to the adjacent loop 20a when in operative position. The cross over location between the straps 20 on the top of the head is adjustable as by providing a pair of mating velcro segments 21 on the engaging cross over surfaces of the respective straps 20 as best shown in FIG. 3.

It will be seen that I have provided a neck and facial lift band assembly which is adjustable to provide the desired lifting of the skin up and away from the mouth and nose areas of the face, upwardly and rearwardly on the lateral jaw portions of the wearer, as well as to provide a lifting of the skin on the front of the neck. The combination of the stretchable under-the-chin segment with the non-stretchable lateral jaw engaging segments produces the controlled lifting of the skin tissue to prevent and remove wrinkles and sagging of the skin.

What is claimed:

1. A neck and facial lift band comprising,
   a chin and jaw engaging yoke assembly which includes: a central stretchable chin engaging segment with a pair of non-stretchable lateral jaw engaging segments extending upwardly from the central stretchable chin engaging segment and contoured to engage the lateral jaw and face portions,
   a lower anchoring neck strap directly connected with an intermediate portion of each lateral jaw engaging segment to surround the rear portion of the upper neck of the wearer and securely anchor the assembly in a horizontal direction,
   a pair of criss cross head engaging straps oriented to pass upwardly over the head of the wearer with the ends thereof respectively anchored to the rear portions of the neck strap and the front ends respectively connected to the upper portions of the jaw engaging segments to provide an upwardly and rearwardly directed lifting action on the engaged jaw and face portions, one end of each of the head engaging straps being provided with a removable connection.

2. The structure set forth in claim 1 wherein the removable connection constitutes a loop and hook connector assembly having means for adjusting the length of each of the criss cross head engaging straps.

3. The structure set forth in claim 1 wherein the lateral segments extend upwardly to approximately the elevation of the ear.

4. The structure set forth in claim 1 and said lower anchoring neck strap being adjustable to permit optimum tensioning on the chin and jaw engaging segments to be obtained in addition to providing lower circumferential anchoring of said segments to the wearer's head.

5. The structure set forth in claim 4 wherein said lower anchoring strap comprising
   a pair of elongated strap segments attached at their forward ends to an intermediate portion of the jaw engaging segments and extending rearwardly therefrom, and means for adjustably anchoring the rear ends of the strap segments together in the desired adjusted position.

6. The structure set forth in claim 1 wherein the criss cross head engaging straps are stretchable.

7. The structure set forth in claim 1 wherein the cross over point of the head straps is adjustable to obtain the required straight-line upward direction of pull on each strap and the length of each strap being adjustable.

8. The structure set forth in claim 1 wherein the non-stretchable jaw engaging segments being formed by laminating non-stretchable material with the stretchable material of the chin engaging segment and said lateral jaw engaging segments being contoured to engage the facial tissue in close proximity to the mouth of the wearer and over the sides of the face to surround and engage the lateral jaw tissue to obtain the desired tissue lifting action upwardly and laterally away from the mouth and upwardly on the lateral jaw skin surfaces, as well as providing a lifting action to skin on neck areas.

* * * * *